United States Patent [19]

Chukwu

[11] Patent Number: 6,033,692
[45] Date of Patent: Mar. 7, 2000

[54] METHOD FOR HYDRATING DRY EDIBLE BEANS

[75] Inventor: Uchenna N. Chukwu, Minnetonka, Minn.

[73] Assignee: Chi's Business Consulting Group, Inc., Minnetonka, Mich.

[21] Appl. No.: 09/196,844

[22] Filed: Nov. 20, 1998

[51] Int. Cl.[7] ............................. A23B 9/08; A23B 7/02; A23B 7/155; A23L 1/20
[52] U.S. Cl. ............................. 426/44; 426/46; 426/52; 426/629
[58] Field of Search .................... 435/187, 209, 435/197, 201, 210; 426/44, 46, 52, 61, 629, 640

[56] References Cited

U.S. PATENT DOCUMENTS 4,333,955  6/1982  Murata et al. ............................. 426/44
5,773,074  6/1998  Veldkamp et al. ....................... 426/615

*Primary Examiner*—Keith D. Hendricks
*Attorney, Agent, or Firm*—Kinney & Lange

[57] ABSTRACT

A method for hydrating dry edible beans comprised of adding an enzyme solution and edible acid to the water in which the beans are soaked. The enzyme consists of a carbo-hydrase and cellulase multi-enzyme complex that is added to an edible acid most commonly vinegar. When soaked in water mixed with the enzyme solution, dry edible beans can achieve approximately 50 percent hydration in approximately two hours. The method of the invention is to create a soak solution by adding an amount of edible acid and enzyme solution to water maintained at the optimal temperature. Beans are added to the soak solution and are soaked for a period of time. The beans are also blanched for five minutes after the soak time. Depending upon the desired results, the pH of the solution, the concentration of enzyme, temperature, and the amount of time can all be varied.

15 Claims, 1 Drawing Sheet

METHOD FOR HYDRATING DRY EDIBLE BEANS

CROSS-REFERENCE TO RELATED APPLICATION(S)

None.

BACKGROUND OF THE INVENTION

Dry edible beans are the dried seeds from plants of the Leguminosae family. Beans supply 20% of the worldwide dietary protein. In the United States, approximately 3.5 billion pounds a year of dry edible beans are produced. Beans are low in fat, cholesterol, and sodium and are high in fiber, complex carbohydrates, and proteins. Beans also contain iron, magnesium, calcium, and phosphorus, present in the form of phytic acid.

In processing dry edible beans, the beans must first be rehydrated. Processing the beans gelatinizes the starches, changes the bean texture, improves the availability of proteins and eliminates toxic substances such as lectins, goitrogenic factors, tannins, and trypsin inhibitors. Processing beans also improves their flavor by making them more palatable.

Dry edible beans are low in moisture, typically having between 12% and 14% moisture content. At 50% moisture, a bean becomes easier to process. Bringing a bean from 12% moisture to about 50% moisture is traditionally accomplished by soaking the beans in water. Water enters the bean through the hilum, and seeps around the periphery of the seed coat, causing it to wrinkle. As time continues, the beans hydrate and expand to yield a smooth swollen bean seed. Two to three cups of water per cup of dried bean is often used for soaking. To speed up the soaking process, the temperature of the water can be raised. In addition, an increased soak temperature also aides in a reduction in the cook time by deactivating the enzyme phytase, which would destroy phytic acid that is used in combination with calcium/magnesium to form the soluble salt that is easy to cook. However, increasing the temperature of the soaking water also increases the loss of calcium, magnesium, thiamin, riboflavin, niacin, and some of the oligosaccharides. Over the years, there have been a variety of alternatives proposed to reduce the soak time. They include pressure processes, vacuum infiltration, ultrasonic sound, gamma irradiation, and a combination of sodium chloride, sodium triphosphate, sodium bicarbonate, sodium carbonate and vacuum infiltration. The high sodium content, the degree of tenderization, and the capital investment have all made these methods unattractive.

Another method is a two minute blanch followed by a long soak after removing the heat source. The increase in the initial soak temperature decreases the overall soak time. Unfortunately, many processing companies do not possess a culinary source of hot water or steam. Furthermore, if the soak water is too hard, containing a large amount of divalent ions, the ions will react with the pectin in the bean to form an insoluble salt, which will increase the time necessary to cook the bean since this insoluble layer will work to minimize the amount of absorbed water. Also observed during the processing of beans is discoloration, skin breakage, the development of off-flavors, and the hard-to-cook phenomenon. The addition of ethylenediaminetetracetic acid (EDTA) has been used to improve the color. Sodium bisulfite has also been added to improve the color, however, it also reduces the availability of vitamin B6. Calcium chloride and citric acid have also been added to improve the firmness, color, and brightness of the bean. However, these compounds have resulted in a reduction in the degree of moisture intake due to their creating a firmer outside on the bean. Acids and the addition of salts containing calcium, magnesium, or aluminum toughen the seed coat and reduce the amount of absorbed water. Lastly, sodium carbonate ($NaHCO_3$) has been added to improve the degree of tenderization by breaking down the hemicellulose, yet it also destroys the B vitamins present.

The food industry has often used enzymes in a variety of situations. Specifically, carbo-hydrase and cellulase enzymes are used in preparations of starch syrups and dextrose, alcohol, beer, ale, fruit juices, chocolate syrups, bakery products, liquid coffee, wine, dairy products, cereals, and spice and flavor extracts. The carbo-hydrase and cellulase enzymes can safely be used in foods.

One carbo-hydrase and cellulase enzyme that is commercially available is Viscozyme® L, a multienzyme complex containing a wide range of carbohydrases. Viscozyme® L can be used to break down cell walls so that useful components can be extracted from plant tissues. This enzyme functions at low temperatures which results in a reduced energy demand and less thermal degradation of the desired materials. Viscozyme® L is particularly useful for processing plant materials in the alcohol, brewing, starch, and related industries. The enzyme has the ability to liberate bound materials and degrade non-starch polysaccharides which improves starch availability in fermentation and reduces viscosity, thus improving yields. The optimum conditions for the activities of this enzyme are a pH of between 3.5 and 5.5, and a temperature of about 40° to 50° C.

BRIEF SUMMARY OF THE INVENTION

Because of the high energy and equipment costs associated with higher temperature soaks, and the high cost and equipment requirements of other hydrating methods, the present invention is a significant improvement in the art in that it greatly reduces soak time while requiring little capital investment to implement. To accomplish this shorter soak time, the present invention is a method for hydrating dry edible beans to approximately 50% moisture by using an enzyme solution while soaking the beans in water. The enzyme solution is made of a cellulase and carbo-hydrase multi-enzyme. Along with the enzyme, an edible acid is added which serves to activate the enzyme. The amount of enzyme depends on the amount of beans and the amount of edible acid is such that the pH of the enzyme solution water is in the range of between 2.0 and 7.0. When using the enzyme, the bean can reach about 50% hydration after only a 2 hour soak.

The method of the present invention is to prepare an enzyme soak solution by weighing an amount of acid and an amount of enzyme. The enzyme solution is added to water to achieve an amount of water solution that is three times the weight of the bean. Beans are added to the water and stirred to ensure a uniform distribution of the enzyme soak solution and the beans. The enzyme soak solution can be maintained at varying temperatures in an effort to speed up the hydrating process. Increasing the temperature increases the rate and degree of hydration. At a low temperature range of 50° to 60° F., the enzyme is not active enough to make a difference in the length of soak time required to hydrate the beans. However, at a mid-range and a high range, the beans do become hydrated at a quicker rate although the difference between the ranges is not significant for some beans.

It is also possible to vary the acidity (pH) and concentration of enzyme in the enzyme solution. An enzyme solution that is 10% by weight of the bean results in a bean that eventually becomes mushy. A concentration of enzyme solution that is 5% by weight of the bean does increase the hydration and decrease the amount of time it takes to hydrate the bean but does not affect the integrity of the bean as much as the 10% solution. However, a 1% solution by weight of the bean works just as well as a 5% solution by weight of the bean. In varying the pH of the solution, the optimal pH range is between is between 3.0 and 6.5. Once the beans are soaked, they are removed from the liquid and drained. After draining, the beans are blanched for five minutes, and are then ready for processing.

DETAILED DESCRIPTION

The present invention is a method of reaching approximately 50% hydration in a dry edible bean in a quick and inexpensive manner. Dry edible beans are the seeds from plants in the Leguminosae family, the most common of which are beans and peas. In hydrating dry edible beans, an enzyme solution is added to the water in which the beans are soaked. The addition of this enzyme greatly reduces the time the dry edible beans must be soaked for them to achieve approximately 50% hydration.

The dry edible beans are hydrated by using a soak solution containing an amount of enzyme, an amount of edible acid to activate the enzyme, and enough water for the soak solution to amount to three times the amount of beans. More specifically, the amount of enzyme used can range from as low as 0.01% to higher than 10% of the weight of the dry edible beans. The amount of edible acid used is enough to bring the soak solution to a pH in the range of between about 2.0 and about 7.0. The temperature of the soak solution preferably ranges from about 40° F. to about 160° F., and the length of the soak can be as long as eight hours to as short as one hour.

The method works best when the amount of enzyme used is closer to 1% of the weight of beans to be hydrated, the pH is between about 4 and about 6, and the temperature is between 110° F. to 120° F. At these conditions, a two hour soak results in close to 50% hydration.

Figure 1:
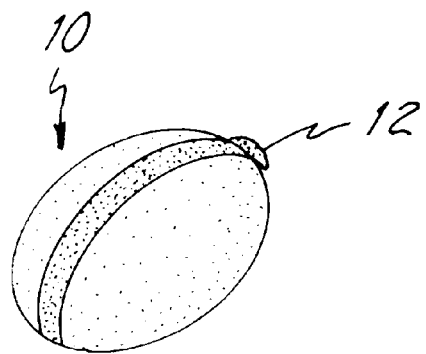
FIG. 1 is a graphical representation of a dry edible bean.

FIG. 1 shows a bean 10 with a hilium 12. Normally, a soaking dry edible bean absorbs the most water through the hilium 12. The hilium 12 is the place the bean 10 was attached to the plant. When soaked in an enzyme solution, the enzyme attacks the outer surface of the bean so that water can enter at places other than the hilium 12.

Figure 2:
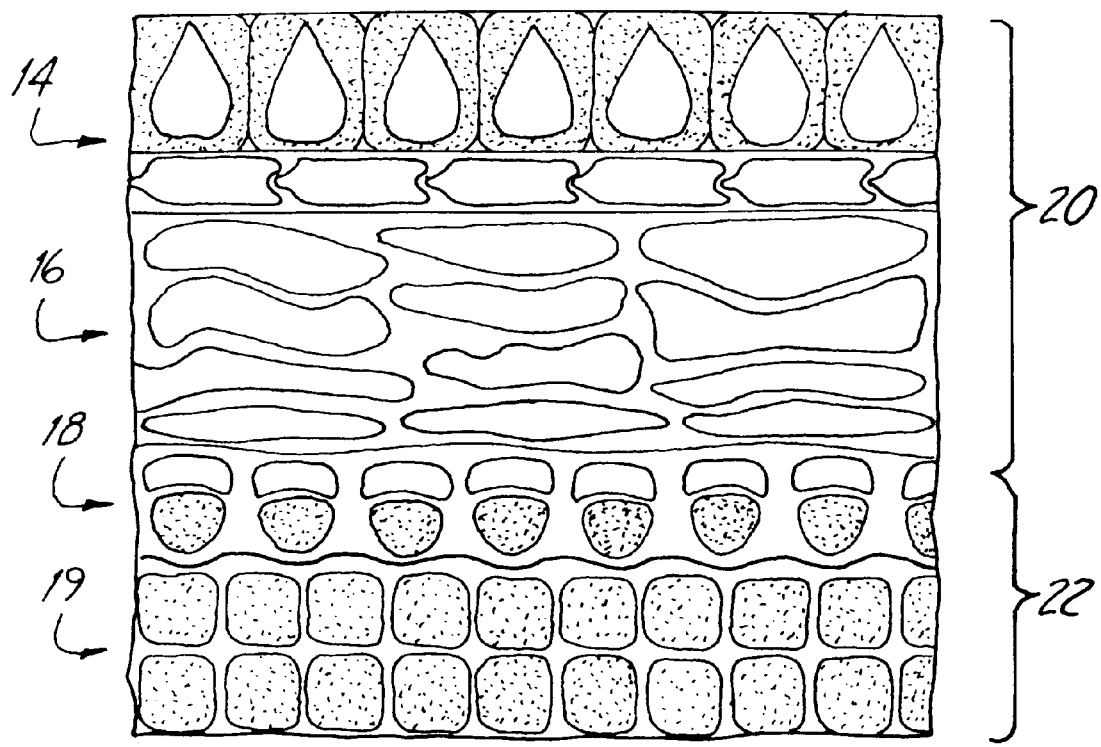
FIG. 2 is a greatly enlarged cross-sectional view of a portion of a bean.

FIG. 2 offers a greatly enlarged view of a cross section of a portion of a dry edible bean. The seed coat 20 consists of several layers of cells, including the outer integument 14 and inner integument 16. Below the seed coat 20 is the cotyledon 22. The cotyledon consists of layers of cells as well, including the epidermis 18. Below the epidermis are the storage parenchyma cells 19.

When soaked in the enzyme solution, the enzyme generates pockets or holes throughout the seed coat 20 through which the water can flow. The water seeps into the seed coat 20, causing the seed coat 20 to pucker or wrinkle. Water continues to flow in and over time, hydrates the cotyledon 22, causing it to swell and fill the seed coat 20. Eventually, the seed coat 20 becomes smooth in appearance, signaling completion of the hydration process. Since the enzymatic solution targets a wide range of insoluble components in the beans, the breakdown of these substances within the bean also serves to tenderize the bean and aid in the reduction of cook time.

Because the enzyme is most active at a lower pH of between 3.5 and 5.5, it is necessary to add an edible acid to the soak water to make the enzyme solution. One such edible acid is vinegar. As mentioned, the amount of soak water to beans is usually in a ratio of 3 to 1. In preparing the soak, an amount of water slightly less than three times the amount of beans to be soaked is prepared and brought to the desired temperature. The edible acid is added to the water, then the enzyme, then the beans, and if necessary, more water is added to bring the amount up to three times the amount of beans to be soaked. Although it is not necessary to prepare the soak solution in this order, doing so ensures that the solution is activated as soon as the enzyme is added and thus is ready when the beans are added.

After soaking the beans in the enzyme solution for about 120 minutes, the beans will have achieved close to 50% moisture. The beans are then blanched. Blanching consists of putting the beans in boiling water for a short time, such as three to five minutes. Blanching serves to further hydrate the bean, as well as deactivate the enzyme and slightly cook the bean, so that processing is easier.

The soak solution can be used as the cook solution, or can be drained away. One reason to drain away the soak solution is that beans can produce flatus, a gas indigestion 5 to 7 hours after consumption. The flatus results from the presence of raffinose and stachyose. Because humans lack alpha-galactosidase in our digestive system, these sugars go undigested and pass into the gut, where micro-organisms degrade the sugars and produce gas. The soak water contains the bulk of these oligosaccharides and thus eliminating it reduces flatus.

The enzyme used in the soak solution is a carbo-hydrase and cellulase type enzyme. These enzymes break down the intercellular and intracellular components of beans that contribute to long soak times. The fibrous network of cellulose, hemicellulose, lignin, and pectin substances that minimize the degree of hydration during bean processing are the substrates of the enzyme complex. Under the proper processing conditions, the enzyme will break down these substances to form celludextrins and glucose. One such enzyme is the carbo-hydrase and cellulase from *Aspergillus niger*. One readily available source of a carbo-hydrase and cellulase form of this enzyme is Viscozyme® L, a multi-enzyme complex containing a wide range of carbo-hydrases. This particular enzyme is prepared from a selected strain of the aspergillus group. Viscozyme® L is a clear brown liquid that is soluble in water and is available in 30 kg or 250 kg steel drums. Viscozyme® L is used in breaking down cell walls for the extraction of useful components from plant tissues and in processing cereal and vegetable materials. The extraction of materials from plant cells can be improved by pretreating the plant material with Viscozyme® L. The enzyme can function at low temperatures, with the optimal conditions for the activity of the enzyme being between 40° and 50° C. with a pH of 3.5 to 5.5. Viscozyme® L does not contain a significant level of amylase or lipase activity so that these major components of plant materials are not affected during the extraction process. In addition, because it can function at lower temperatures, there is a reduced energy demand and less thermal degradation of the desired materials. Viscozyme® L is currently used in processing plant materials in the alcohol, brewing, starch, and related industries. The enzyme is fit for human consumption.

The carbo-hydrase solution used to obtain the data below has the declared enzymes: arabinase, cellulase, beta-glucanase, hemicellulase, and xylanase. Other carbo-hydrase solutions may also contain the following enzyme systems: alpha-amylase, pectinase, pectin depolymerase, pectin methyl esterase, pectin lyase, glucomylase, oligo-1, 6 glucosidase, hemicellulase, lactase, beta-gluconase, beta-glucosidase and alpha-galactosidase. Other sources of carbohydrase and cellulase enzymes suitable for this invention are Cytolase® and Rapidase® systems, which are all available from Gist-Brocade.

Several variables affect how quickly the beans can be hydrated. First of all, the amount of enzyme per weight of the bean can be varied. If the amount of enzyme used is 1% of the weight of dry edible beans, the effect is satisfactory. If the amount of enzyme is increased to 5% of the weight of the bean, the same amount of hydration is achieved in the same amount of time. If the amount of enzyme is increased to 10% of the weight of the bean, certain undesirable events occur. At the 10% solution of enzyme, the outer shell of the bean becomes too porous. When the outer shell becomes too porous, the beans float and stop absorbing water. In addition, increasing the concentration of enzyme increases the degree of cook in the bean, so at 10% solution, the beans may end up mushy when processed after the soak.

The amount of edible acid can also be varied. However, increasing the acidity of the soak water does not significantly impact the rate of hydration. A very low pH creates an unacceptable taste in the beans and results in the beans looking less hydrated and more puckered. The higher the pH, the more hydrated the beans look and the greater the degree of cook in the kernel, as observed by the greater degree of translucency at the outer edges of the bean. A pH above 7 results in losing some of the vitamins present in the bean. The pH level can be varied somewhat in relation to how the beans will ultimately be processed. If the beans are added to a tomato sauce, for instance, the effect on taste from a lower pH will not be as noticeable.

Temperature can also be varied; the beans can be soaked at a low temperature range of 50° to 60° F., a mid temperature range of 110° to 120° F., and a high temperature range of 150° to 160° F. Beans can be soaked at a constant temperature, but it is also possible to start the soak at a low temperature and increase the temperature of the soak as time progresses. Increasing the temperature increases the rate and degree of hydration. However, there is not a vast degree of difference between the mid range and high range in temperature for some of the beans. The low temperature range is too low and does not appear to affect the hydration of the beans. In addition, the outer shell remains tough and fibrous and is only minimally transformed at low temperatures.

The length of time the beans are soaked in the enzyme solution and water also affects the hydration of the beans. When soaked for 120 minutes, the degree of hydration is higher than when the beans are soaked for 60 minutes.

To illustrate the effect of concentration of enzyme, acidity, temperature, and time several experiments were performed. In performing the experiments, vinegar was added to an amount of water which was then brought to temperature. It was after the vinegar was added and the water brought to temperature that the enzyme was added. This order was necessary to make sure that the enzyme was not affected during the time it would take to bring water to temperature and was an attempt to make sure that the water solution would be activated as soon as the enzyme was added. Once the enzyme was added to the prepared water and vinegar solution, the beans were added and this mixture was stirred. As soon as the beans were added a timer was set. The temperature and pH were measured at 15 minute intervals during the 1hour soak, and at half-hour intervals during the 2 hour soaks. At the end of the soak period, the beans were drained on paper towels for five minutes, were weighed, and were placed into boiling water for a five-minute blanch. After the blanch, the beans were again drained on paper towels and again weighed. The percent hydration achieved was determined by the following formula:

$$\frac{weight_{final} - weight_{initial}}{weight_{final}} 100$$

In all experiments, temperatures were taken with a digi-sense thermometer from Cole Parmer, Model No. 91100-00, Probe J; temperatures were maintained between a certain temperature range by using a Cole-Parmer Ceramic Top Hot Plate Model No. 034001-10 and a Whirlpool Freestanding Range, Model No. RF365BXPN. A Frigidaire refrigerator Model No. F44N21CED3 was also utilized in maintaining the lower temperatures. The pH of the samples was measured using a Cole-Parmer 59002-02 PH/MV/temp meter. The pH 4.01 buffer was supplied by Cole-Parmer 05942-20. The pH 7.00 buffer was supplied by Cole-Parmer 05942-40. The weight of the samples was measured by an Acculab V6 kg scale also obtained from Cole-Parmer. The edible acid was vinegar supplied by Best Yet and Gedney. Calcium chloride was supplied by Spectrum of Gardenia, Calif. (Cole-Parmer). The calcium chloride was anhydrous granular and FCC grade. The beans were obtained from a local grocery store except for pink, red and green/yellow lima beans which were obtained from Friday Canning Corporation located in Ackley, Iowa.

The results of the experiments are shown in the tables below. The experiments for each type of bean were randomized and repeated twice to ensure reproducibility.

TABLE 1

| Bean | Temp (in ° F.) | pH | Concent. (% by wgt of beans) | % Hydration |
|---|---|---|---|---|
| Navy(1) | 110–120 | 4.00 | 10% | 41.6 |
| Navy(2) | 110–120 | 4.00 | 10% | 43.1 |
| Navy(1) | 110–120 | 4.00 | 5% | 43.3 |
| Navy(2) | 110–120 | 4.00 | 5% | 43.6 |
| Navy(1) | 110–120 | 4.00 | 1% | 44.2 |
| Navy(2) | 110–120 | 4.00 | 1% | 42.4 |

Table 1 shows the effect of varying the concentration of the enzyme in the soak solution. Two hundred and fifty grams of navy beans were soaked for 60 minutes in enzyme solutions of varying concentration. The temperature was maintained between 110° and 120° F. and the target pH was around 4.00. The concentration of enzyme used was either 1%, 5%, or 10% of the weight of the beans used. As can be seen, the degree of hydration varied from 41.6% to 44.2%. At a 10% concentration, the hydration was not significantly higher than a 1% or 5% concentration. At a 1% by weight of the bean concentration, the beans achieved similar hydration rates as a 5% concentration.

TABLE 2

| Bean | Temp (in ° F.) | pH | Concent. (% by wgt of beans) | % Hydration |
|---|---|---|---|---|
| Pinto(1) | 50–60 | 4.00 | 5% | 35.2 |
| Pinto(2) | 50–60 | 4.00 | 5% | 33.2 |
| Pinto(1) | 110–120 | 4.00 | 5% | 43.4 |
| Pinto(2) | 110–120 | 4.00 | 5% | 42.9 |
| Pinto(1) | 150–160 | 4.00 | 5% | 46.4 |
| Pinto(2) | 150–160 | 4.00 | 5% | 44.8 |

Table 2 shows the effect of varying the temperature of the soak solution. Two hundred and fifty grams of pinto beans were soaked in a soak solution which had a pH of 4.00 and a concentration of enzyme of 5% per weight of the bean. The time of the soak was 60 minutes. As can be seen by the percent of hydration, as the temperature range was increased, the degree of hydration increased.

TABLE 3

| Bean | Temp (in ° F.) | pH | Concent. (% by wgt of beans) | % Hydration |
|---|---|---|---|---|
| Great Northern (1) | 110–120 | 2.7 | 5% | 45.7 |
| Great Northern (2) | 110–120 | 2.93 | 5% | 39.9 |
| Great Northern (1) | 110–120 | 4.00 | 5% | 48.4 |
| Great Northern (2) | 110–120 | 4.00 | 5% | 44.4 |
| Great Northern (1) | 110–120 | 6.5 | 5% | 47.4 |
| Great Northern (2) | 110–120 | 6.36 | 5% | 44.7 |

Table 3 shows the effect of varying the pH when soaking 250 grams of great northern beans for 60 minutes. The temperature was maintained between 110° and 120° F., and the concentration of enzyme was 5% per weight of the bean. As can be seen, the results are quite variable. Please note that at the lower pH, the beans acquire a very acidic taste that is unacceptable.

TABLE 4

| Bean | Ave. Temp. (in ° F.) | Initial pH | Concent. (% by wgt of bean) | Time (in minutes) | % Hydration |
|---|---|---|---|---|---|
| Light Red Kidney | 118.0 | 4.0 | 1.20 | 120 | 49.9 |
| Pinto Bean | 117.9 | 4.0 | 1.20 | 120 | 48.4 |
| Blackeye Pea | 120.1 | 4.1 | 1.20 | 120 | 54.8 |
| Pinks | 115.6 | 4.0 | 1.20 | 120 | 45.3 |
| Great Northern Bean | 119.2 | 3.9 | 1.20 | 120 | 48.1 |
| Navy Beans | 117.9 | 4.0 | 1.20 | 120 | 44.9 |
| Green/Yellow Lima | 120.8 | 4.0 | 1.20 | 120 | 48.5 |
| Red Beans | 122.5 | 4.0 | 1.20 | 120 | 44.1 |
| Garbanzo | 149.6 | 4.2 | 1.20 | 120 | 46.8 |
| Black Beans | 147.3 | 4.0 | 1.20 | 120 | 46.4 |

Table 4 shows the percent hydration achieved after a 120 minute soak for a variety of beans. The variety of beans chosen reflects their popularity in the U.S. market. Temperature was kept between 110° and 120° F. and was recorded every 30 minutes. The temperature value in the table is an average of those recorded temperatures. The garbanzo and black beans were kept at a slightly higher temperature range, as is evident from the average temperature. The initial pH was targeted for around 4, because as the soak progresses, the pH rises. The concentration of enzyme was 1.2% per weight of bean. After 2 hours, the percent of hydration ranged from between 44.1% for red beans to 54.8% for black-eyed peas. The garbanzo and black beans, which were soaked at a higher temperature, achieved a percent of hydration at 46.8% and 46.4% respectively.

TABLE 5

| Bean | Ave Temp. (in ° F.) | Initial pH | Concent. (% wgt. of bean) | Time (in min.) | % Hydration | Control 4 HR/ 150 |
|---|---|---|---|---|---|---|
| Light Red Kidney | 141 | 5.1 | 1.2 | 120 | 53 | 50 |
| Pinto Bean | 138 | 4.9 | 1.2 | 120 | 51 | 54 |
| Blackeye | 136 | 5.1 | 1.2 | 120 | 52 | 54 |
| Pinks | 136 | 4.9 | 1.2 | 120 | 48 | 50 |
| Great Northern Bean | 146 | 5.1 | 1.2 | 120 | 52 | 53 |
| Navy Beans | 134 | 5.2 | 1.2 | 120 | 50 | 46 |
| Green/Yellow Lima | 140 | 4.9 | 1.2 | 120 | 53 | 53 |
| Red Beans | 141 | 5.1 | 1.2 | 120 | 50 | 50 |
| Garbanzo | 138 | 5.2 | 1.2 | 120 | 49 | 53 |
| Black Beans | 139 | 5.1 | 1.2 | 120 | 49 | 49 |

Table 5 shows the data collected after soaking 250 grams of various beans for 120 minutes at a slightly higher pH and temperature. Temperature was measured at half hour intervals throughout the 120 minute soak. These values were then averaged to get the value shown in the table. Once again, pH is an initial pH since the pH will slightly rise over the period of the soak. The concentration of enzyme was 1.2% of the weight of the bean. As can be seen, the percent hydration for the variety of beans ranged from 48% for pinks up to 53% for light red kidney beans and green-yellow lima beans. The last column shows the percent hydration from a four hour control soak of 250 grams of the same type of beans.

Although the present invention has been described with reference to preferred embodiments, workers skilled in the art will recognize that changes may be made in form and detail without departing from the spirit and scope of the invention.

I claim:

1. A method for hydrating dry edible beans to prepare them for processing, the method comprising:

providing a quantity of dry edible beans having a hydration of less than about 14% soaking the quantity of dry edible beans in an enzyme solution maintained at a temperature of between about 40° F. and 160° F. for a period of time sufficient for the beans to reach at least 40% hydration, the enzyme solution including water, an amount of edible acid to bring the water and edible acid to a pH of between about 2.0 and about 7.0, and a carbohydrase and cellulase enzyme;

removing the beans from the water, enzyme, and edible acid solution and draining the beans; and blanching the beans to deactivate the enzyme solution.

2. The method of claim 1 wherein the water and enzyme mixture and beans are maintained at a temperature greater than about 110° F. during the soak.

3. The method of claim 1 wherein the water and enzyme mixture and beans are maintained at a temperature between about 110° F. and about 120° F. during the soak.

4. The method of claim 1 wherein the water and enzyme mixture and beans are maintained at a temperature above about 40° F. during the beginning of the soak and the temperature of the water and enzyme mixture and beans is gradually increased during the soak to less than about 160° F.

5. The method of claim 1 and further comprising returning the blanched beans to the water, enzyme, and edible acid solution for further processing.

6. The method of claim 1 wherein the enzyme solution includes an amount of enzyme that is at least about 0.01% of the weight of the beans, and an edible acid such that the water and enzyme mixture has a pH of between about 4 and about 5.

7. The method of claim 1 wherein the enzyme solution includes an amount of enzyme that is at least about 0.01% of the weight of the beans, and an edible acid such that the water and enzyme mixture has a pH of less than about 4.

8. The method of claim 1 wherein the enzyme solution includes an amount of enzyme that is at least about 0.01% of the weight of the beans, and on edible acid such that the water and enzyme mixture has a pH of greater than about 5.

9. The method of claim 1 wherein the enzyme solution includes an amount of enzyme that is between about 1% and about 10% of the weight of the beans, and an edible acid such that the water and enzyme mixture has a pH of between about 4 and about 5.

10. The method of claim 1 wherein the enzyme solution includes an amount of enzyme that is between about 1% and about 10% of the weight of the beans, and an edible acid such that the water and enzyme mixture has a pH of less than about 4.

11. The method of claim 1 wherein the enzyme solution includes an amount of enzyme that is between about 1% and about 10% of the weight of the beans, and an edible acid such that the water and enzyme mixture has a pH of greater than about 5.

12. The method of claim 1 and further comprising stirring the water, enzyme, and edible acid solution and beans to ensure a uniform distribution.

13. The method in claim 1 wherein the blanching lasts between about 3 minutes and about 8 minutes.

14. The method of claim 1 wherein the enzyme solution comprises:

an amount of enzyme that is about 0.01% to about 10% of the weight of the beans that will be hydrated; and an amount of water sufficient to achieve a ratio of 3 to 1 of the weight of the beans to be hydrated.

15. The enzyme solution of claim 14 wherein the edible acid is vinegar.

* * * * *